United States Patent [19]

Otten et al.

[11] Patent Number: 4,950,984

[45] Date of Patent: Aug. 21, 1990

[54] APPARATUS FOR DETERMINING THE PROPORTION OF A SUBSTANCE HAVING PARAMAGNETIC PROPERTIES IN A MIXTURE OF SUBSTANCES

[75] Inventors: Johann Otten, Bad Schwartau; Scato Albarda, Gross Schenkenberg; Hansjochen Schuck, Stockelsdorf, all of Fed. Rep. of Germany

[73] Assignee: Drägerwerk Aktiengesellschaft, Lübeck, Fed. Rep. of Germany

[21] Appl. No.: 319,965

[22] Filed: Mar. 7, 1989

[30] Foreign Application Priority Data

Nov. 30, 1988 [DE] Fed. Rep. of Germany ....... 3840337

[51] Int. Cl.$^5$ ..................... G01N 27/74; G01R 33/12
[52] U.S. Cl. ..................................... 324/204; 73/27 A
[58] Field of Search .............. 324/204, 228, 239, 262; 73/27 R, 27 A

[56] References Cited

U.S. PATENT DOCUMENTS

| | | | |
|---|---|---|---|
| 2,467,211 | 4/1949 | Hornteck | 324/204 |
| 2,689,332 | 9/1954 | Greene | 324/204 |
| 2,763,509 | 8/1988 | Albarda et al. | 324/204 X |
| 2,903,883 | 9/1959 | Luft | 73/27 A |
| 3,076,929 | 2/1963 | Gillerman | 324/204 |
| 3,539,913 | 11/1970 | Prival | 324/204 |
| 3,714,557 | 1/1973 | Gast | 324/204 |
| 3,742,344 | 6/1973 | Hummel | 73/27 A X |
| 4,808,922 | 2/1989 | Eder et al. | 324/204 |

FOREIGN PATENT DOCUMENTS 59-147252 8/1984 Japan ..................... 324/204
2184846 7/1987 United Kingdom .

Primary Examiner—Reinhard J. Eisenzopf
Assistant Examiner—Warren S. Edmonds
Attorney, Agent, or Firm—Walter Ottesen

[57] ABSTRACT

The invention is directed to an apparatus for determining the proportion of substances having paramagnetic characteristics, such as oxygen, in a mixture of substances. The apparatus has a housing and the mixture of substances is passed along an arrangement of four magnetic field sources by a rotatable cuvette arrangement mounted in the housing. The apparatus is improved in that the effect of external disturbing influences on the penetration of the cuvette by the magnetic field is reduced and so that the measuring characteristics are independent of the position of the plurality of magnetic field generating units. For this purpose, the arrangement of the magnetic field sources is simply disposed at one side of the housing lying opposite to the rotating surface of the cuvette arrangement facing toward the drive shaft. The arrangement of magnetic field sources includes a carrier plate on which the magnetic field sources are accommodated and carry respective measuring field coils. The magnetic field sources face with their end faces toward the cuvette arrangement.

11 Claims, 3 Drawing Sheets

APPARATUS FOR DETERMINING THE PROPORTION OF A SUBSTANCE HAVING PARAMAGNETIC PROPERTIES IN A MIXTURE OF SUBSTANCES

FIELD OF THE INVENTION

The invention relates to an apparatus for determining the proportion of substances having paramagnetic characteristics, such as oxygen, in a mixture of substances. The apparatus includes a housing and a rotatable cuvette arrangement in which the mixture of substances is passed along an arrangement of four or a higher even multiple of magnetic field sources. Each of the magnetic field sources includes a coil arrangement for converting the magnetic flux changes caused therein by the paramagnetic substance into an electric measuring signal. The magnetization polarization of the magnetic field sources are combined with the magnetization polarization of the measuring field coils corresponding thereto in alternating alignment to each other.

BACKGROUND OF THE INVENTION

An apparatus of the kind described above is disclosed in U.S. Pat. No. 4,808,922.

The known arrangement of magnetic field sources comprises four or a higher even multiple of magnets or magnetic field coils which are accommodated in a housing on both sides of the rotating end faces of a rotatable cuvette arrangement.

Each of the magnetic field sources is surrounded by a coil which can receive the changes of the magnetic field produced by the paramagnetic material and transmit the changes to an evaluation device. The direction of the magnetic fields of the magnetic field sources and measuring coils is matched alternately to each other so that disturbances caused by stray fields or by microphony are compensated for. An especially precise alignment of the magnetic field sources and measuring field coils lying opposite each other is necessary because the measuring result is essentially dependent upon the penetration of the measuring cuvette by the magnetic force lines. The smallest deviations become noticeable as a different flux density which leads to undesired fluctuations of the measured value. Furthermore, it is necessary to provide for the rotation of the measuring cuvette so that it is free of vibration to the extent that a complex journalling of the drive shaft is required which provides a precise fit.

During rotation of the cuvette, the field lines of the magnetic field sources penetrate the individual cuvette sections in different proportions. The magnetic field sources of constant flux thereby penetrate the individual measuring sections of the cuvette arrangement with a different magnetic potential during a rotational movement. This leads to the condition that the measuring signal increases from a low value to a maximum value as soon as the maximum magnetic potential is reached when the measuring cuvette enters into the magnetic field and decreases in a corresponding manner when the measuring cuvette leaves the magnetic field. These signal fluctuations require additional complexity with respect to the processing of the measured value insofar as fluctuations in the measured value are to be eliminated. Stray fields arise because the drive shaft passes through the arrangement of the magnetic field sources and these stray fields are usually caused by the metal drive shaft. The stray fields rotate with the cuvette and likewise falsify the measuring result.

SUMMARY OF THE INVENTION

It is an object of the invention to provide an apparatus for determining paramagnetic characteristics of substances of the kind described above which is improved so that the effect of external disturbing influences on the penetration of the cuvette by the magnetic field is reduced. It is a further object of the invention to provide such an apparatus wherein the measuring characteristics are independent of the position of the plurality of magnetic field generating devices relative to each other with the entire measuring apparatus being simpler and easier to assemble. Furthermore, the apparatus according to the invention enables the penetration of the cuvette by the magnetic fields to be as constant as possible while the cuvette rotates.

The apparatus of the invention includes a housing and an arrangement of magnetic field sources. The arrangement of magnetic field sources is disposed in the housing on only one end thereof and opposite the rotating surface of the cuvette which faces away from the drive shaft. The arrangement of magnetic field sources includes a carrier plate on which the magnetic field sources carrying the measuring field coils are accommodated. The magnetic field sources have respective end faces facing toward the cuvette arrangement.

With the one-sided arrangement of the magnetic field sources at one end of the housing, a complex assembly and alignment of the different sources and measuring field coils with respect to each other is no longer required.

A disturbance by rotating stray fields is prevented since the drive shaft does not extend through the magnetic fields. A drive unit can be provided which contains the drive motor having the shaft and the cuvette firmly mounted on this shaft. The assembly of such an apparatus is simple in that the separate drive block is combined with a separate magnetic field part which permits both the drive block and the magnetic field part to be optimized with respect to the respective functions which they perform. In this way, signal fluctuations in the course of a measurement are reduced and a higher mechanical stability is obtained for the rotational frequencies which are quite high.

An especially favorable cuvette arrangement comprises a circular disc which has cutouts formed therein which are symmetrical with respect to the axis of rotation. The cutouts are configured such that for a position of one of the cutouts in which the end face of one of the magnetic field sources is fully exposed, the end face of the next adjacent magnetic field source remains excluded from the region within the contour of this cutout and the sum of the cross sections of the end faces which are only partly exposed by the cutout contours remains essentially constant. A configuration of the cuvette as described above makes it possible that an approximately constant penetration of the measuring cuvette is obtained at every point in time of the rotational movement. When one of the magnetic field sources appears completely in the cutout, the next adjacent magnetic field source is still completely covered. As soon as the end face of the magnetic field source in view becomes partially covered because of the advancing rotational movement of the cuvette, a corresponding portion of the next adjacent magnetic field source is exposed by the advancing cutout. In this way, the magnetic field sources act as magnetic sources of constant magnetic potential which is a precondition for the largest possible measurement signal.

The magnetic field sources are preferably cores made of magnetizable material which can be attached to the carrier plate configured as a disc-shaped magnet plate. Measuring field coils corresponding to respective ones of these sources are then wound about the cores. Another embodiment of the magnetic field sources can include current coils which are mounted on the carrier plate and are surrounded by the measuring field coils.

An especially advantageous form of the cutout contours is provided by circular annular segments extending concentrically about the rotational axis. These annular segments are so dimensioned that they fully expose the end faces of the magnetic field sources when passing over the latter during the rotational movement of the cuvette.

A cutout contour as good as the one described above is provided by a kidney-shaped cutout extending concentrically to the rotational axis.

If magnetizable cores are mounted as magnetic field sources on a disc-shaped permanent magnet, then an improvement of the equipotential characteristics can be obtained when the cores are connected via a plate functioning as an equipotential disc and made of good magnetically-conducting material.

A suitable material for this purpose has been shown to be a highly permeable iron-cobalt alloy for the equipotential disc.

In order to obtain a still higher harmonic decoupling between the drive unit for the cuvette arrangement and the magnetic field sources, the drive housing is provided with labyrinth-like wall portions whose harmonic decoupling prevents a sound conducted through solids from being transmitted to the magnetic field sources.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
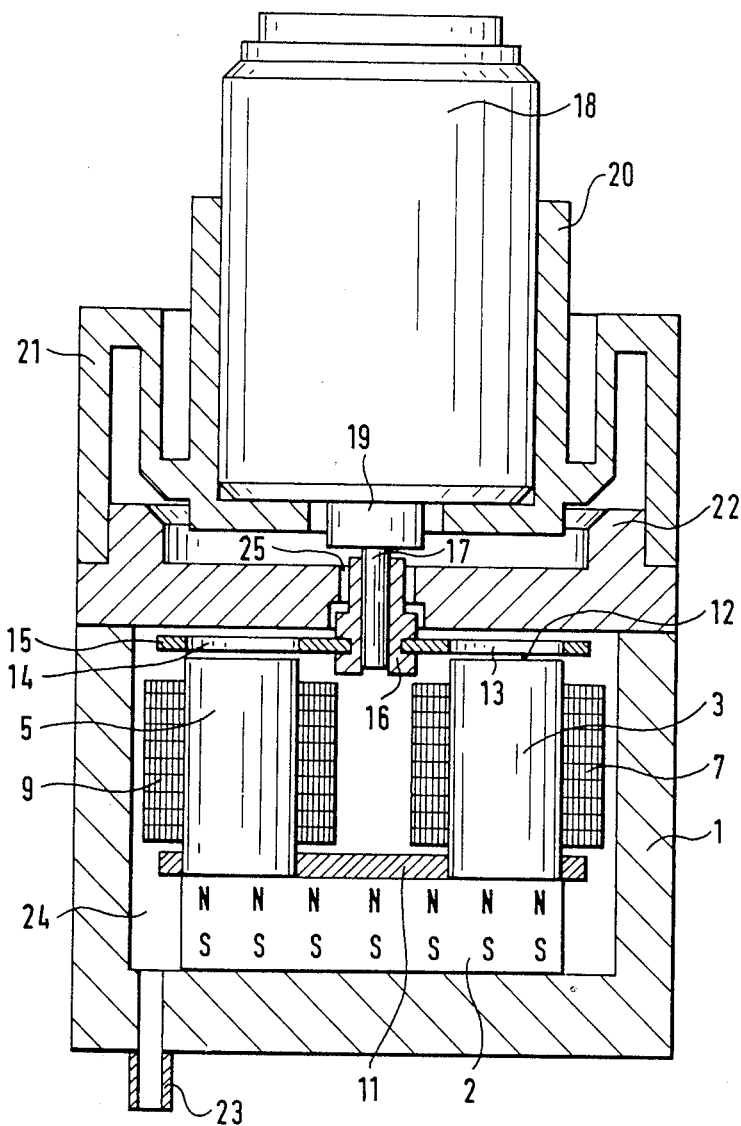
FIG. 1 is a side elevation view, in section, of a paramagnetic measuring apparatus according to the invention.

FIG. 1 shows an apparatus housing 1 in which a magnetic plate 2 is provided as a carrier for iron cores (3, 5). The iron cores (3, 5) are connected with each other via an equipotential plate 11. The polarization of the magnetic plate 2 is indicated by the symbols N and S. The cores (3, 5) are enclosed by measuring field coils (7, 9) corresponding to respective ones thereof. The end faces 12 of the cores (3, 5) face in a direction toward the cutouts (13, 14) of a disc-shaped cuvette arrangement 15. The cuvette 15 is mounted on a shaft collar 16 which is attached to the shaft 17 of a drive motor 18 and is guided in a shaft bearing 19. Motor 18 and the motor mount 20 are attached to base wall 22 via a labyrinth-shaped wall portion 21.

The gas to be tested is supplied via a gas feed 23 which communicates with the measuring chamber 24. The chamber 24 extends into the region of rotation of the cuvette 15 and from there leads to the ambient via an outlet 25 and a further outlet (not shown) in wall portion 21 through which the gas can pass to the ambient.

Figure 2:
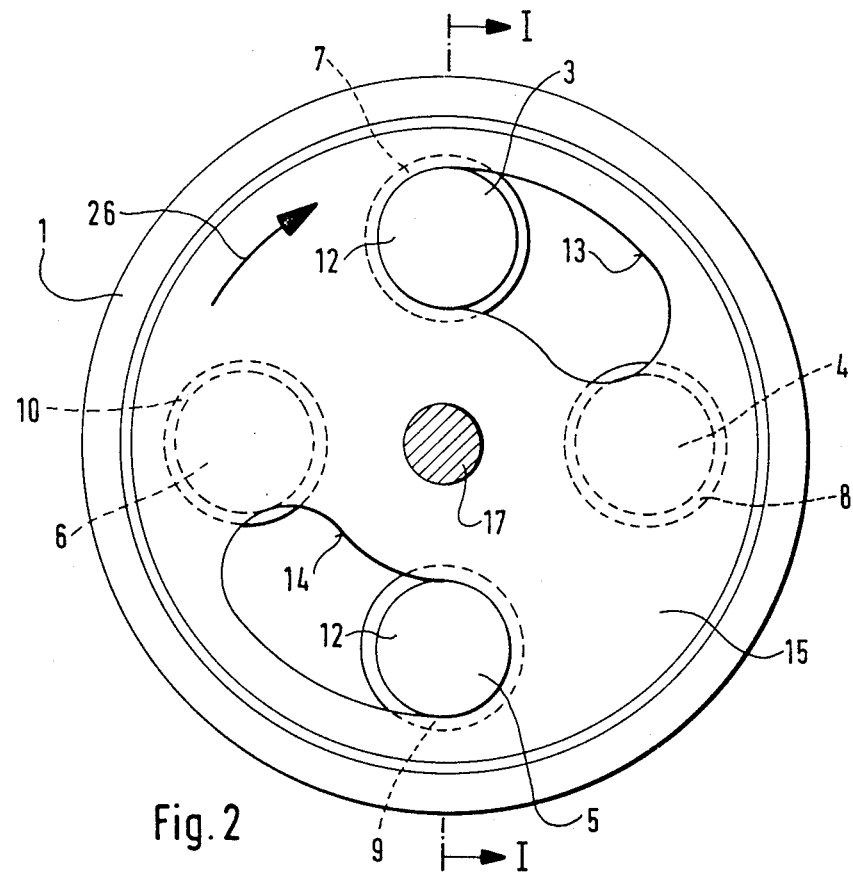
FIG. 2 is a plan view of the cuvette arrangement of the apparatus of FIG. 1 with the drive unit removed.

The drive unit comprises the motor 18 and the motor mount 20 having the labyrinth wall portion 21. FIG. 2 is a plan view showing the cuvette arrangement 15 with the drive unit removed. The cuvette 15 is mounted in the housing 1 via the shaft 17 for rotation in the direction of arrow 26. The cuvette 15 is configured as a disc and has two cutouts (13, 14) which are approximately kidney-shaped and lie axially opposite each other. The end faces 12 of the cores (3, 5) are fully exposed by the cutouts for the position of the cuvette shown in FIG. 2. The corresponding next adjacent cores (4, 6) are just barely visible within the contour of the respective cutouts (13, 14) but are not yet exposed. With the rotation of the cuvette 15 in the direction of arrow 26, the cores (3, 5) are reduced with respect to the flux which can freely pass through the cutouts (13, 14) and the end faces of the cores (4, 6) become increasingly exposed in a corresponding amount. In this way, the continuous reduction of flux of the magnetic fields because of the advancing covering of the cores (3, 5) is substantially compensated by the magnetic fields of the cores (4, 6) which become ever more exposed in the cutouts (13, 14).

Figure 3:
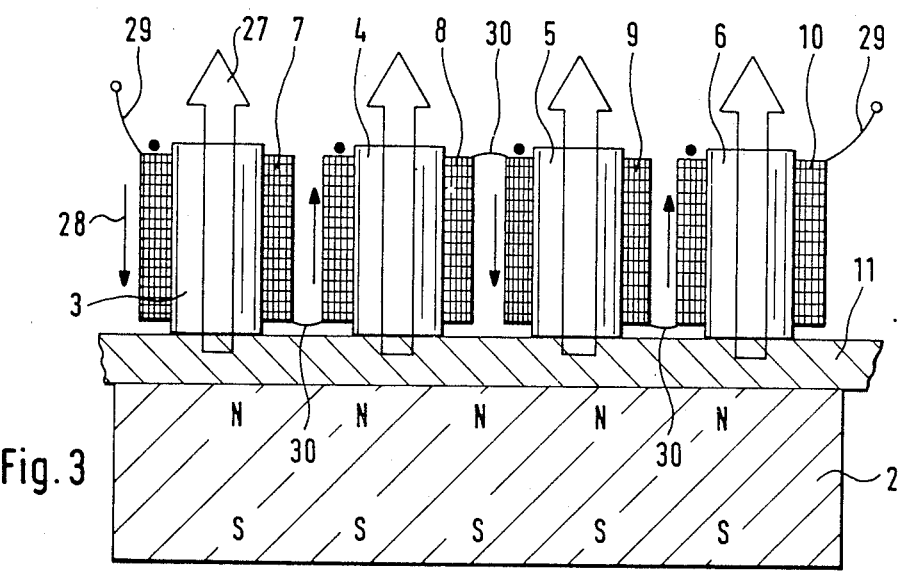
FIG. 3 is a schematic representation showing the winding directions of the measuring field coils corresponding to respective ones of the magnetic field sources; and, FIG. 4 shows the waveforms of magnetic flux and the measurement signals which are generated.

By means of the alternate winding directions of the measuring field coils (3, 5) on the one hand, and of the measuring field coils (4, 6) on the other hand, as shown schematically in FIG. 3, the reductions in flux produced in the coils (7, 9) generates a positive voltage because of the fading penetration of the magnetic fields through the paramagnetic substance. Because of the reversed winding sense in the coils (8, 10), the increase in flux produced there likewise leads to a positive voltage because of the amplification of the flux increase through the cutouts (13, 14). In this way, a total signal which remains essentially constant is obtained from the measuring signals of the four individual coils (7, 8, 9, 10) because of the flux which remains constant.

FIG. 3 shows a schematic cut-away portion of the embodiment illustrated in FIG. 1 with the magnetic field plate 2 and the equipotential plate 11 lying thereon being shown. The cores (3, 4, 5, 6) having respective measuring field coils (7, 8, 9, 10) are also illustrated. The flux direction in the cores (3, 4, 5, 6) is indicated by respective arrows 27. The winding sense of the measuring field coils (7, 8, 9, 10) is indicated by the solid dot shown on the coil body with the flux direction of the measuring field produced in the measuring field coils (7, 8, 9, 10) being illustrated by the narrow arrow 28. The signal is taken off at the signal lines 29 with the individual measuring field coils (7, 8, 9, 10) being connected to each other via connecting lines 30.

Figure 4:
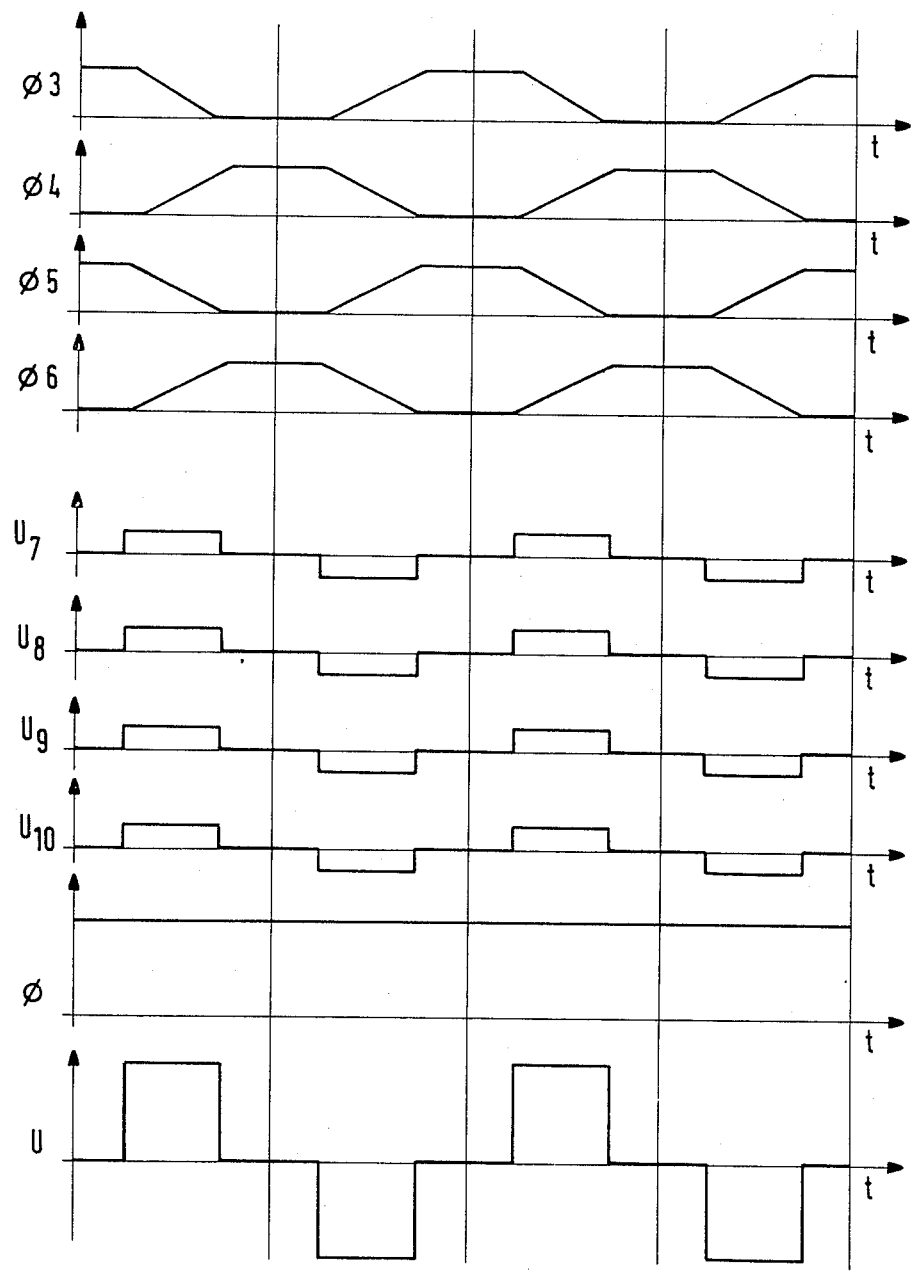

FIG. 4 shows schematically the time change of the magnetic flux $\phi_3$ to $\phi_6$ for the individual cores (3, 4, 5, 6) with the corresponding individual voltage signals $U_7$ to $U_{10}$ generated in the measuring field coils (7, 8, 9, 10) as well as the time dependent course of the total flux $\phi$ and the total voltage U taken off at the signal lines 29. The time t defines the course of the rotational movement of the cuvette 15.

It is understood that the foregoing description is that of the preferred embodiments of the invention and that various changes and modifications may be made thereto without departing from the spirit and scope of the invention as defined in the appended claims.

What is claimed is:

1. Apparatus for the determining the proportion of a substance having paramagnetic properties in a mixture of substances, the apparatus comprising:

a housing defining a longitudinal axis and having a first longitudinal end and a second longitudinal end opposite said first longitudinal end;

a cuvette arrangement disposed between said longitudinal ends and having a plurality of cells for receiving the mixture of substances containing the substance having the paramagnetic properties;

four magnetic field sources for providing respective magnetic fields for penetrating said cuvette arrangement;

said cuvette arrangement defining a rotational axis extending along said longitudinal axis and being rotatably mounted in said housing for rotating said mixture in said cells through said magnetic fields whereby said paramagnetic substance causes magnetic flux changes;

said cuvette arrangement having first and second rotating surfaces facing toward said first and second longitudinal ends of said housing, respectively;

a drive unit mounted at said first longitudinal end of said housing so as to face toward said first surface of said cuvette arrangement and having a drive shaft operatively connected to said cuvette arrangement for rotatably driving the same about said rotational axis;

a carrier plate disposed in the region of said second longitudinal end of said housing;

said four magnetic field sources having respective end faces;

said magnetic field sources being mounted on said carrier plate so as to cause said end faces to face toward said second rotating surface and permit the cuvette arrangement and said cells to pass by above said end faces;

said drive shaft being mounted in said housing so as to be arranged between said first longitudinal end and said cuvette arrangement so as to avoid extending through said magnetic fields; and each of said magnetic field sources including a measuring field coil for converting said magnetic flux changes into a electrical signal.

2. The apparatus of claim 1, each of said magnetic field sources having a magnetization polarization and the measuring field coil corresponding to each of said sources likewise having a magnetization polarization; and, each two mutually adjacent ones of said sources having alternate alignments of the two polarizations associated with each source.

3. The apparatus of claim 2, the number of said magnetic field sources being an even multiple greater than said four magnetic field sources.

4. The apparatus of claim 3, said cuvette arrangement comprising a circular disc having cutouts defining said cells; and, said cutouts being positioned in said circular disc so as to be symmetrical to said rotational axis and said cutouts having respective contours configured such that for a position of one of the cutouts in which the end face of one of the magnetic field sources is fully exposed, the end face of the next adjacent magnetic field source remains excluded from the region within the contour of said one cutout; and, said contours being further configured such that the sum of the cross sections of the end faces which are only partly exposed by the contours of said cutouts remains essentially constant in the course of the rotational movement of said circular disc.

5. The apparatus of claim 4, said carrier plate being a magnetic plate and each of said magnetic field sources including respective iron cores attached to said magnetic plate; and, said measuring field coils being wound about corresponding ones of said iron cores.

6. The apparatus of claim 4, said cutouts being circular annular segmented cutouts concentric to said rotational axis.

7. The apparatus of claim 4, said cutouts having a kidney-shaped contour and extending concentrically to said rotational axis.

8. The apparatus of claim 5, comprising an equipotential plate made of good magnetically conducting material and being interposed between said iron cores and said magnetic plate for interconnecting said iron cores; and, said magnetic plate being mounted on said equipotential plate.

9. The apparatus of claim 8, said good magnetically conducting material being a highly permeable iron-cobalt alloy.

10. The apparatus of claim 1, said drive unit including a motor for driving said drive shaft; and, mounting means for mounting said motor on said housing.

11. The apparatus of claim 10, said mounting means being a labyrinth-shaped wall interconnecting said motor and said housing.

* * * * *